United States Patent [19]

Van Lommen et al.

[11] Patent Number: 4,654,362

[45] Date of Patent: Mar. 31, 1987

[54] DERIVATIVES OF 2,2'-IMINOBISETHANOL

[75] Inventors: Guy R. E. Van Lommen, Berlaar; Marcel F. L. De Bruyn, Hoogstraten; Marc F. J. Schroven, Heist Op Den Berg, all of Belgium

[73] Assignee: Janssen Pharmaceutica, N.V., Beerse, Belgium

[21] Appl. No.: 660,355

[22] Filed: Oct. 12, 1984

Related U.S. Application Data

[63] Continuation-in-part of Ser. No. 558,081, Dec. 5, 1983, abandoned.

[51] Int. Cl.$^4$ .................... A61K 31/35; A61K 31/34; C07D 311/58; C07D 307/87

[52] U.S. Cl. .................................. 514/452; 549/404; 549/407; 549/389; 549/361; 549/387; 549/433; 549/458; 549/467; 514/454; 514/456; 514/463; 514/468; 514/469

[58] Field of Search ............... 549/400, 401, 404, 407, 549/389, 392, 394, 361, 387, 334, 433, 458, 466, 467; 260/239 B, 239 BE, 239 BF; 514/452, 454, 456, 463, 468, 469

[56] References Cited

U.S. PATENT DOCUMENTS 4,313,955  2/1982  Huebner et al. ..................... 549/366
4,380,653  4/1983  Huebner et al. ..................... 549/366

OTHER PUBLICATIONS

Howe et al., J. Med. Chem., 13, 169 (1970).

Primary Examiner—Nicky Chan
Attorney, Agent, or Firm—Geoffrey G. Dellenbaugh

[57] ABSTRACT

Derivatives of 2,2'-iminobisethanol having useful properties in the treatment and/or the prevention of disorders of the coronary-vascular system.

12 Claims, No Drawings

DERIVATIVES OF 2,2'-IMINOBISETHANOL

CROSS-REFERENCE TO RELATED APPLICATIONS

This is a continuation-in-part of our co-pending application Ser. No. 558,081, filed Dec. 5, 1983, now abandoned.

BACKGROUND OF THE INVENTION 1,5-Bis-(1,4-benzodioxin-2-yl)-3-azapentan-1,5-dioles having β-adrenergic blocking agents have been described in J. Med. Chem. 13, (2), 169–176 (1970) and specific stereochemically isomeric forms of said 1,5-dioles have been described in U.S. Pat. Nos. 4,380,653 and 4,313,955.

The compounds of the present invention differ from the said prior art compounds by the replacement of one oxygen atom in the benzodioxane ring by a direct bond or an optionally substituted methylene moiety and by their increased β-adrenergic blocking activity.

DESCRIPTION OF THE PREFERRED EMBODIMENTS

The present invention is concerned with derivatives of 2,2'-iminobisethanol having the formula:

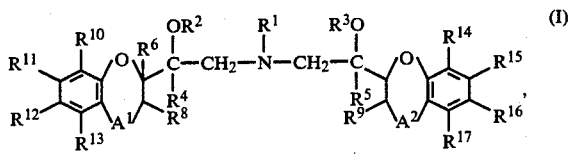

the pharmaceutically acceptable acid addition salts and the stereochemically isomeric forms thereof, wherein $R^1$ is hydrogen, $C_{1-6}$ alkyl, aryl, aryl-$C_{1-6}$ alkyl, $C_{1-12}$ alkylcarbonyl or arylcarbonyl;

$R^2$ and $R^3$ are each independently hydrogen, $C_{1-12}$ alkylcarbonyl or arylcarbonyl;

$R^4$, $R^5$, $R^6$ and $R^7$ are each independently hydrogen or $C_{1-6}$ alkyl;

$A^1$ and $A^2$ are each independently a direct bond, —$CH_2$—, >C=O or a functional derivative thereof, >C=S, >CH—OH or >CH—O—CO($C_{1-12}$ alkyl);

$R^8$ and $R^9$ are hydrogen or the radical —$A^1$—CH$R^8$— and/or the radical —$A^2$—CH$R^9$— may each represent an 1,2-ethenediyl radical; and $R^{10}$, $R^{11}$, $R^{12}$, $R^{13}$, $R^{14}$, $R^{15}$, $R^{16}$ and $R^{17}$ are each independently hydrogen, halo, $C_{1-6}$ alkyl, $C_{2-6}$ alkenyl, $C_{2-6}$ alkynyl, $C_{1-6}$ alkyloxy, $C_{2-6}$ alkenylmethoxy, $C_{1-6}$ alkylthio, trifluoromethyl, hydroxy, amino, mono or di($C_{1-6}$ alkyl)amino, arylamino, (aryl $C_{1-6}$ alkyl)amino, cyano, nitro, aryl, aryloxy, aryl $C_{1-6}$ alkyloxy, $C_{1-6}$ alkyloxy-$C_{1-6}$ alkyl or a radical of formula

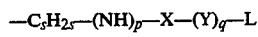 (a)

said s being 0 or an integer of from 1 to 6 inclusive;
said p and q being independently 0 or the integer 1;
said X being >C=O; >C=S; or

said Y being NH or O; and said L being hydrogen, $C_{1-6}$ alkyl, aryl or aryl-$C_{1-6}$ alkyl; or two vicinal radicals of $R^{10}$, $R^{11}$, $R^{12}$ and $R^{13}$ and of $R^{14}$, $R^{15}$, $R^{16}$ and $R^{17}$ may complete an aromatic-, alicyclic-, dioxanyl- or dioxolanyl ring;

provided that not more than two radicals of $R^{10}$, $R^{11}$, $R^{12}$ and $R^{13}$ or of $R^{14}$, $R^{15}$, $R^{16}$ and $R^{17}$ are amino, mono- or di($C_{1-6}$ alkyl)amino, arylamino, (aryl-$C^{1-6}$ alkyl)amino, nitro, aryl, aryloxy or a radical of formula (a);

wherein aryl as used in the foregoing definitions is phenyl optionally substituted with up to three substituents each independently selected from the group consisting of halo, lower alkyl, lower alkyloxy, lower alkylthio, trifluoromethyl, nitro and amino; and wherein the functional derivatives of >C=O are oximes, hydrazones, di(lower alkyl)ketals, a dioxolane- or dioxane ring and the corresponding dithioketals.

As used in the foregoing definitions the term halo is generic to fluoro, chloro, bromo and iodo; $C_{1-6}$ alkyl is meant to include straight and branch chained saturated hydrocarbon radicals having from 1 to 6 carbon atoms such as, for example, methyl, ethyl, 1-methylethyl, 1,1-dimethylethyl, propyl, 2-methylpropyl, butyl, pentyl, hexyl and the like; $C_{1-12}$ alkyl is meant to include $C_{1-6}$ alkyl and the higher homologs thereof having from 7 to 12 carbon atoms; $C_{2-6}$ alkenyl is meant to include alkenyl radicals having from 2 to 6 carbon atoms, such as, for example, 2-propenyl, 2-butenyl, 3-butenyl, 2-pentenyl and the like; $C_{2-6}$ alkynyl is meant to include alkynyl radicals having from 2 to 6 carbon atoms, such as, for example, 2-propynyl, 2-butynyl, 3-butynyl, 2-pentynyl and the like.

Preferred compounds within the invention are those wherein $A^1$ and $A^2$ are each independently a direct bond or a —$CH_2$— radical. Other preferred compounds within the invention are those wherein no more than two of $R^{10}$–$R^{17}$ are other than hydrogen.

The most preferred compounds is α,α'-[iminobis(methylene)]bis[3,4-dihydro-2H-1-benzopyran-2-methanol], a pharmaceutically acceptable acid addition salt thereof or a stereochemically isomeric from thereof.

In order to simplify the structural representations of the compounds (I) and of a number of starting materials and intermediates used in the preparation thereof, the radical

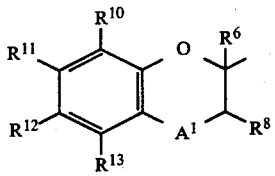

will hereinafter be represented by the symbol $D^1$ while the radical

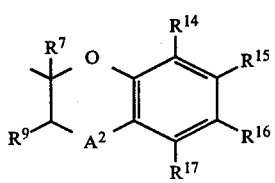

will hereinafter be represented by the symbol $D^2$.

The compounds of formula (I) may generally be prepared by N-alkylating an amine of formula (II-a) or (II-b) with an intermediate of formula (III-a) respectively (III-b) following art-known N-alkylating procedures.

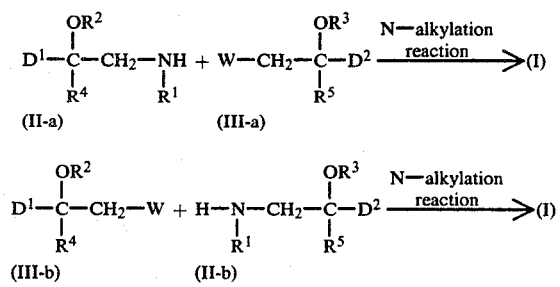

In (III-a) and (III-b) W represents an appropriate reactive leaving group such as, for example, halo, e.g., chloro, bromo or iodo, or a sulfonyloxy group, e.g. methylsulfonyloxy or 4-methylphenylsulfonyloxy.

It is evident from the structure of the intermediates of formulae (III-a) and (III-b) that in the particular case where $R^3$ respectively $R^2$ is hydrogen the said reagents may previously be converted into the corresponding oxiranes having the formula

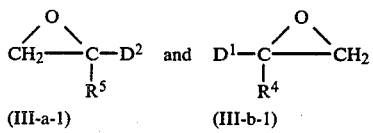

or that the said oxiranes as such are used as intermediates.

The alkylation reactions are conveniently conducted in an inert organic solvent such as, for example, an aromatic hydrocarbon, e.g., benzene, methylbenzene, dimethylbenzene, and the like; a lower alkanol, e.g., methanol, ethanol, 1-butanol and the like; a ketone, e.g., 2-propanone, 4-methyl-2-pentanone and the like; and ether, e.g., 1,4-dioxane, 1,1'-oxybisethane, tetrahydrofuran and the like; N,N-dimethylformamide (DMF); N,N-dimethylacetamide (DMA); nitrobenzene; 1-methyl-2-pyrrolidinone; and the like. The addition of an appropriate base such as, for example, an alkali metal carbonate or hydrogen carbonate, sodium hydride or an organic base such as, for example, N,N-diethylethanamine or N-(1-methylethyl)-2-propanamine may be utilized to pick up the acid which is liberated during the course of the reaction. In some circumstances the addition of an iodide salt, preferably an alkali metal iodide, is appropriate. Somewhat elevated temperatures may enhance the rate of the reaction.

The compounds of formula (I) can also be converted into each other following art-known procedures of functional group transformation. Some examples will be cited hereinafter.

The compounds of formula (I) having a nitro substituent can be converted into their corresponding amines by stirring and, if desired, heating the starting nitro-compounds in a hydrogen-containing medium in the presence of a suitable amount of an appropriate catalyst such as, for example, platinum-on-charcoal, palladium-on-charcoal, Raneynickel and the like catalysts. Suitable solvents are, for example, alcohols, e.g., methanol, ethanol and the like.

The compounds of formula (I) wherein $R^1$ is a phenylmethyl radical can be converted into the compounds of formula (I) wherein $R^1$ is hydrogen following art-known hydrogenolysis procedures.

The compounds of formula (I) wherein $R^2$ and/or $R^3$ is/are hydrogen may be converted into the corresponding compounds of formula (I) wherein $R^2$ and/or $R^3$ is/are $C_{1-12}$ alkylcarbonyl or arylcarbonyl by reacting the former compounds with an appropriate carboxylic acid or a suitable functional derivative thereof.

In all of the foregoing and in the following preparations, the reaction products may be isolated from the reaction mixture and, if necessary, further purified according to methodologies generally known in the art.

The compounds of formula (I) have basic properties and, consequently, they may be converted to their therapeutically active non-toxic acid addition salt forms by treatment with appropriate acids, such as, for example, inorganic acids, such as hydrohalic acid, e.g. hydrochloric, hydrobromic and the like, and sulfuric acid, nitric acid, phosphoric acid and the like; or organic acids, such as, for example, acetic, propanoic, hydroxyacetic, 2-hydroxypropanoic, 2-oxopropanoic, ethanedioic, propanedioic, butanedioic, (Z)-2-butenedioic, (E)-2-butenedioic, 2-hydroxybutanedioic, 2,3-dihydroxybutanedioic, 2-hydroxy-1,2,3-propanetricarboxylic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids. Conversely the salt form can be converted by treatment with alkali into the free base form.

From formula (I) it is evident that the compounds of this invention may have several asymmetric carbon atoms in their structure. Each of these chiral centers may be present in a R- and a S-configuration, this R- and S-notation being in correspondence with the rules described in J. Org. Chem. 35 (9), 2849–2867 (1970).

Pure stereochemically isomeric forms of the compounds of formula (I) may be obtained by the application of art-known procedures. Diastereoisomers may be separated by physical separation methods such as selective crystallization and chromatographic techniques, e.g., counter current distribution, and enantiomers may be separated from each other by the selective crystallization of their diastereomeric salts with optically active acids.

Pure stereochemically isomeric forms may also be derived from the corresponding pure stereochemically isomeric forms of the appropriate starting materials, provided that the reaction occurs stereospecifically.

It is evident that the stereochemically isomeric forms may be further resolved into their optical isomers, (+) and (−) by the application of methodologies known to those skilled in the art. Stereochemically isomeric forms of the compounds of formula (I) are naturally intended to be embraced within the scope of the invention.

In many compounds and starting materials the stereochemical configuration is not experimentally determined. In those cases it is conventionally agreed to designate the stereochemically isomeric form which is first isolated as "A" and the second as "B", without further reference to the actual stereochemical configuration.

For the most preferred compound, α,α'-[iminobis(methylene)]bis[3,4-dihydro-2H-1-benzopyran-2-methanol], it has experimentally been determined that the "A" form corresponds with the RS or SR configuration at the chiral centers 1 and 2 or 3 and 4 while the "B" form corresponds with the SS or RR configuration at the said chiral centers.

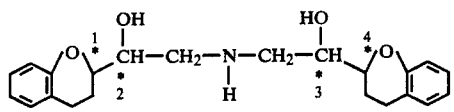

A number of intermediates and starting materials in the foregoing preparations are known compounds which may be prepared according to art-known methodologies of preparing said or similar compounds. A number of such preparation methods will be described hereinafter in more detail.

The intermediates of formulae (II-a) and (II-b) may generally be prepared by reacting an amine of formula (IV) with a reagent of formula (III-b) respectively (III-a) following the same procedure as previously described herein for the preparation of the compounds of formula (I).

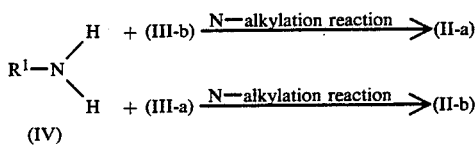

In a number of particular cases the reaction of (IV) with (III-b) or (III-a) and the consequent reactions of the thus formed (II-a) or (II-b) with a reagent (III-a) or (III-b), thus yielding the desired compound of formula (I), may be conducted during the same N-alkylation reaction procedure.

As it is described for the preparation of the compounds of formula (I) the intermediates of formula (III-a) and (III-b) may also previously be converted into the corresponding oxiranes having the formulae (III-a-1) and (III-b-1) or said oxiranes may be used as such as intermediates.

The intermediates of formulae (III-a-1) and (III-b-1) may be prepared following art-known procedures for preparing oxiranes, e.g. by epoxidizing a corresponding alkene or by reacting an appropriate aldehyde with a suitable reagens, such as a trimethylsulfoxonium halide or a trimethylsulfonium halide.

The intermediates of formulae (III-a-1) and (III-b-1) are new and as useful intermediates in the preparations of the compounds of formula (I) they constitute an additional feature of the present invention.

The compounds of formula (I) and their pharmaceutically acceptable acid addition salts and stereochemically isomeric forms possess strong β-adrenergic receptor blocking activity and as such they can be used in the treatment and prevention of disorders of the coronary vascular system.

Due to their useful β-adrenergic receptor blocking activity and, more particularly, in view of their selective $β_1$-adrenergic receptor blocking activity, combined with their vasodilating properties, resulting in a useful antihypertensive activity, the compounds of formula (I), the pharmaceutically acceptable acid addition salts and the stereochemically isomeric forms thereof are useful agents in the treatment and the prevention of disorders of the coronary vascular system.

In view of their useful properties in the treatment and the prevention of disorders caused by the coronary vascular system the subject compounds may be formulated into various pharmaceutical forms for administration purposes. To prepare the pharmaceutical compositions of this invention an effective amount of the particular compound or compounds, in base or acid-addition salt form, as the active ingredient, is combined in intimate admixture with a pharmaceutically acceptable carrier, which carrier may take a wide variety of forms depending on the form of preparation desired for administration, said amount being an amount which is effective to normalize irregular cardial rhythms. These pharmaceutical compositions are desirable in unitary dosage form suitable, preferably, for administration orally, rectally or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, may be prepared in which the carrier comprises saline solution, glucose solution or a mixture of saline and glucose solution. Injectable suspensions may also be prepared in which case appropriate liquid carriers, suspending agents and the like may be employed. Acid addition salts of (I), due to their increased water solubility over the corresponding base form, are obviously more suitable in the preparation of aqueous compositions.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof. The amount of active ingredient per dosage unit is from about 0.25 mg to about 1000 mg and, preferably from about 0.5 to about 500 mg.

In view of the usefulness of the subject compounds in the treatment and the prevention of disorders of the coronary vascular system it is evident that the present invention provides a method of treating and/or preventing disorders caused by the coronary system in vertebrates by the systemic administration of an effective amount of at least one compound of formula (I), an acid addition salt or a stereochemically isomeric form thereof in admixture with a suitable amount of a pharmaceutically acceptable carrier.

The following examples are intented to illustrate and not to limit the scope of the present invention. Unless otherwise stated all parts therein are by weight.

EXPERIMENTAL PART

A. Preparation of Intermediates

EXAMPLE 1

To a stirred mixture of 80 parts of 6-bromo-3,4-dihydro-2H-benzopyran-2-carboxylic acid and 225 parts of tetrahydrofuran were added dropwise 400 parts of a solution of borane, compound with thiobismethane 0.2N in tetrahydrofuran. Upon completion, stirring was continued for 4hours at room temperature. 80 parts of methanol were added dropwise and stirring was continued for 30 minutes at reflux temperature. The solvent was distilled off till half its volume. The remaining solvent was evaporated and the residue was distilled, yielding 63 parts (86%) of 6-bromo-3,4-dihydro-2H-1-benzopyran-2-methanol; bp. 150° C. at 39.9 Pa (intermediate 1).

A mixture of 297 parts of 6-bromo-3,4-dihydro-2H-1-benzopyran-2-methanol and 108 parts of copper (I) cyanide in 450 parts of N,N-dimethylformamide was stirred and refluxed for 4 hours. The reaction mixture was poured onto a solution of 600 parts of iron chloride in 180 parts of hydrochloric acid and 1000 parts of water. The whole was stirred for 20 minutes at 60° C. The aqueous phase was extracted with methylbenzene. The extract was filtered over Hyflo. The filtrate was washed successively with 10% hydrochloric acid, water, 10% sodium hydroxide and again with water, filtered again, dried and evaporated, yielding 112 parts (49.3%) of 3,4-dihydro-2-(hydroxymethyl)-2H-1-benzopyran-6-carbonitrile; mp. 85° C. (intermediate 2).

A mixture of 40 parts of 3,4-dihydro-2-(hydroxymethyl)-2H-1-benzopyran-6-carbonitrile in 200 parts of sodium hydroxide solution 20% was stirred and refluxed overnight. The reaction mixture was poured onto water and the product was extracted with 1,1'-oxybisethane. The aqueous phase was separated and filtered. The filtrate was acidified, whereupon the product was precipitated, yielding 40 parts (90%) of 3,4-dihydro-2-(hydroxymethyl)-2H-1-benzopyran-6-carboxylic acid; mp. 150° C. (intermediate 3).

To a stirred solution of 40 parts of 3,4-dihydro-2-(hydroxymethyl)-2H-1-benzopyran-6-carboxylic acid in 400 parts of methanol were added a few drops of sulfuric acid. Stirring was continued overnight at reflux. The reaction mixture was evaporated. The residue was taken up in 1,1'-oxybisethane. The whole was washed with a sodium hydroxide solution 10% and with water, dried, filtered and evaporated, yielding 24 parts (53.9%) of methyl 3,4-dihydro-2-(hydroxymethyl)-2H-1-benzopyran-6-carboxylate as a residue (intermediate 4).

EXAMPLE 2

A mixture of 63.4 parts of 6-fluoro-4-oxo-4H-1-benzopyran-2-carboxylic acid and 400 parts of acetic acid was hydrogenated at normal pressure and at room temperature with 3 parts of palladium-on-charcoal catalyst 10%. After the calculated amount of hydrogen was taken up, the catalyst was filtered off and the filtrate was evaporated. The residue was stirred in petroleum ether. The product was filtered off and dried in vacuo at about 70° C., yielding 49 parts (83.3%) of 6-fluoro-3,4-dihydro-2H-1-benzopyran-2-carboxylic acid (intermediate 5).

During 2 hours, gaseous hydrogen chloride was bubbled through a stirred mixture of 50 parts of 6-fluoro-3,4-dihydro-2H-1-benzopyran-2-carboxylic acid and 1200 parts of ethanol at reflux temperature. After cooling, the reaction mixture was evaporated. The residue was taken up in a mixture of 1,1'-oxybisethane and a sodium hydroxide solution. The organic layer was separated, washed with water, dried, filtered and evaporated, yielding 58.8 parts (100%) of ethyl 6-fluoro-3,4-dihydro-2H-1-benzopyran-2-carboxylate as a residue (intermediate 6).

To a stirred mixture of 50 parts of ethyl 6-fluoro-3,4-dihydro-2H-1-benzopyran-2-carboxylate and 540 parts of benzene were added dropwise, during a 1 hour-period, a mixture of 89 parts of a solution of sodium dihydro-bis(2-methoxyethoxy)aluminate in methylbenzene (3.4M) and 135 parts of benzene at reflux temperature and under nitrogen atmosphere. Upon completion, stirring was continued for 2.5 hours at reflux. After cooling to 15° C., the reaction mixture was decomposed by the dropwise addition of 24 parts of ethanol and 10 parts of water. The reaction mixture was poured onto ice water. Concentrate hydrochloric acid and 350 parts of 1,1'-oxybisethane were added. The organic layer was separated, washed with water, dried, filtered and evaporated. The oily residue was purified by column chromatography over silica gel using trichloromethane as eluent. The pure fractions were collected and the eluent was evaporated, yielding 34 parts (85%) of 6-fluoro-3,4-dihydro-2H-1-benzopyran-2-methanol as an oily residue (intermediate 7).

EXAMPLE 3

To a stirred mixture of 11.1 parts of 3,4-dihydro-6-nitro-2H-1-benzopyran-2-carboxylic acid and 63 parts of tetrahydrofuran were added dropwise, during a 30 minutes-period, 23.6 parts of a borane dimethyl sulfide complex solution 2M in tetrahydrofuran (slightly exothermic reaction: temp. rose to 27° C.). Upon completion, the whole was heated to reflux and stirring was continued for 2 hours at reflux temperature. The reaction mixture was decomposed by the dropwise addition of 8 parts of methanol at reflux temperature. After stirring and refluxing for 10 minutes, the solvents were distilled off and the residue was taken up in water. The solution was treated with concentrate hydrochloric acid and extracted with 1,1'-oxybisethane. The extract was washed with water, dried, filtered and evaporated. The solid residue was suspended in warm 2,2'-oxybispropane. The product was filtered off and dried, yielding 7.0 parts (70%) of 3,4-dihydro-6-nitro-2H-1-benzopyran-2-methanol; mp. 96.5° C. (intermediate 8).

To a stirred mixture of 38 parts of 3,4-dihydro-6-nitro-2H-1-benzopyran-2-methanol, 30 parts of 3,4-dihydro-2H-pyran and 750 parts of trichloromethane were added 3 drops of 2-propanol saturated with hydrogen chloride (slightly exothermic reaction). The whole was stirred for 3 hours in a water bath at room temperature. The whole was washed with a cold sodium hydroxide solution 10% and with water. The organic layer was dried, filtered and evaporated. The oily residue was purified by column chromatography over silica gel using trichloromethane as eluent. The pure fractions were collected and the eluent was evaporated. The oily residue was solidified in petroleumether. The product was filtered off and dried, yielding 34 parts (64%) of 3,4-dihydro-6-nitro-2-[[(tetrahydro-2H-pyran -2-yl)oxy]methyl]-2H-1-benzopyran; mp. 66.4° C. (intermediate 9).

A mixture of 34 parts of 3,4-dihydro-6-nitro-2-[[(tetrahydro-2H-pyran-2-yl)oxy]methyl]-2H-1-benzopyran, 1 part of a solution of thiophene in methanol 4% and 200 parts of methanol was hydrogenated at normal pressure and at room temperature with 2 parts of palladium-on-charcoal catalyst 10%. After the calculated amount of hydrogen was taken up, the catalyst was filtered off and the filtrate was evaporated, yielding 31 parts (100%) of 3,4-dihydro-2-[[(tetrahydro-2H-pyran-2-yl)oxy]methyl]-2H-1-benzopyran-6-amine as an oily residue (intermediate 10).

To a stirred mixture of 5.3 parts of 3,4-dihydro-2-[[(tetrahydro-2H-pyran-2-yl)oxy]methyl]-2H-1-benzopyran-6-amine and 50 parts of pyridine were added dropwise 2.25 parts of acetic acid anhydride at a temperature below 10° C. Upon completion, stirring was continued for 10 minutes in an ice bath. The whole was stirred for 3 hours at room temperature. The reaction mixture was evaporated. Water was added to the residue. The product was extracted with 1,1'-oxybisethane. The organic layer was washed with water, dried, filtered and evaporated, yielding 5 parts (82%) of N-[3,4-dihydro-2-[[(tetrahydro-2H-pyran-2-yl)oxy]methyl]-2H-1-benzopyran-6-yl]-acetamide as an oily residue (intermediate 11).

To a stirred solution of 27 parts of N-[3,4-dihydro-2-[[(tetrahydro-2H-pyran-2-yl)oxy]methyl]-2H-1-benzopyran-6-yl]-acetamide in 240 parts of methanol were added 100 parts of a hydrochloric acid solution 10% in water. The whole was stirred for 30 minutes at room temperature. The reaction mixture was evaporated till all traces of methanol were removed. After cooling, the product was filtered off from the aqueous phase, washed with water and crystallized from acetonitrile. The product was filtered off and dried, yielding 14.4 parts (74%) of N-[3,4-dihydro-2-(hydroxymethyl)-2H-1-benzopyran-6-yl]acetamide; mp. 156.5° C. (intermediate 12).

EXAMPLE 4

A mixture of 61 parts of 6-methoxy-4-oxo-4H-1-benzopyran-2-carboxylic acid and 500 parts of acetic acid was hydrogenated at normal pressure and at room temperature with 5 parts of palladium-on-charcoal catalyst 10%. After the calculated amount of hydrogen was taken up, the catalyst was filtered off and the filtrate was evaporated. The residue was stirred in petroleumether. The product was filtered off and dried in vacuo at about 65° C., yielding 49.1 parts (84.2%) of 3,4-dihydro-6-methoxy-2H-1-benzopyran-2-carboxylic acid; mp. 140° C. (intermediate 13).

In a similar manner there were also prepared:
3,4-dihydro-7-methyl-2H-1-benzopyran-2-carboxylic acid (intermediate 14); and
3,4-dihydro-5,7-dimethyl-2H-1-benzopyran-2-carboxylic acid (intermediate 15).

EXAMPLE 5

To a stirred mixture of 109 parts of 3,4-dihydro-5,7-dimethyl-2H-1-benzopyran-2-carboxylic acid in 135 parts of tetrahydrofuran were added, during a period of 20 minutes, 292 parts of a solution of borane, compound with thiobismethane, in tetrahydrofuran 2M (foaming). The whole was stirred and refluxed for 2 hours. The mixture was decomposed by the addition of 24 parts of methanol. After stirring for 10 minutes at reflux temperature, the solvent was distilled off. Water was added to the residue. Concentrate hydrochloric acid was added and the product was extracted with 1,1'-oxybisethane. The organic layer was washed with water and sodium chloride, dried, filtered and evaporated, yielding 97.5 parts (96%) of 3,4-dihydro-5,7-dimethyl-2H-1-benzopyran-2-methanol as an oily residue (intermediate 16).

Following the same procedure and using equivalent amounts of the appropriate starting materials, there were also prepared:
3,4-dihydro-7-methyl-2H-1-benzopyran-2-methanol (intermediate 17); and
3,4-dihydro-6-methoxy-2H-1-benzopyran-2-methanol (intermediate 18).

EXAMPLE 6

A mixture of 12 parts of 4-oxo-4H-naphtho[1,2-b]pyran-2-carboxylic acid and 100 parts of 2-methoxyethanol was hydrogenated at normal pressure and at room temperature with 2 parts of palladium-on-charcoal catalyst 10%. After the calculated amount of hydrogen was taken up, the catalyst was filtered off and the filtrate was evaporated, yielding 7 parts (61.4%) of 3,4-dihydro-2H-naphtho[1,2-b]pyran-2-carboxylic acid as a residue (intermediate 19).

In a similar manner there was also prepared:
3,4,7,8,9,10-hexahydro-2H-naphtho[1,2-b]pyran-2-carboxylic acid (intermediate 20).

EXAMPLE 7

A mixture of 60 parts of 3,4-dihydro-6-hydroxy-2H-1-benzopyran-2-carboxylic acid, 800 parts of ethanol and 5.52 parts of concentrate sulfuric acid was stirred for 3 hours at reflux temperature. The reaction mixture was evaporated. Water was added and the product was extracted with trichloromethane. The extract was washed with water, dried, filtered and evaporated. The residue was purified by column chromatography over silica gel using a mixture of trichloromethane and methanol (95:5 by volume) as eluent. The pure fractions were collected and the eluent was evaporated. The residue was solidified in petroleumether. The product was filtered off and dried, yielding 48 parts (70%) of ethyl 3,4-dihydro-6-hydroxy-2H-1-benzopyran-2-carboxylate as a residue (intermediate 21).

EXAMPLE 8

30 Parts of 3,4-dihydro-2H-1-benzopyran-2-carboxylic acid were added slowly, during a 30 minutes-period, to 79 parts of a solution of nitric acid 60% while cooling on an ice bath. The whole was stirred for 10 minutes at room temperature. The reaction mixture was poured onto ice water. The product was extracted with trichloromethane. The extract was dried, filtered and evaporated. The residue was purified by column chromatography over silica gel using a mixture of trichloromethane and methanol (90:10 by volume) as eluent. The pure fractions were collected and the eluent was evaporated. The residue was crystallized from a mixture of ethanol and water (80:20 by volume), yielding 17 parts (45%) of 3,4-dihydro-6-nitro-2H-1-benzopyran-2-carboxylic acid; mp. 180° C. (intermediate 22).

A mixture of 60 parts of 3,4-dihydro-6-nitro-2H-1-benzopyran-2-carboxylic acid, 480 parts of ethanol and 5.52 parts of concentrate sulfuric acid was stirred for 2 hours at reflux temperature. The reaction mixture was evaporated. The residue was crystallized from 2,2'-oxybispropane (activated charcoal). The product was filtered off and dried, yielding 65 parts (95%) of ethyl 3,4-dihydro-6-nitro-2H-1-benzopyran-2-carboxylate; mp. 80.8° C. (intermediate 23).

A mixture of 59.8 parts of ethyl 3,4-dihydro-6-nitro-2H-1-benzopyran-2-carboxylate, 3 parts of a solution of thiophene in methanol 1% and 480 parts of methanol was hydrogenated at normal pressure and at room temperature with 5 parts of palladium-on-charcoal catalyst 10%. After the calculated amount of hydrogen was taken up, the catalyst was filtered off and the filtrate was evaporated, yielding 48 parts (90%) of ethyl 6-amino-3,4-dihydro-2H-1-benzopyran-2-carboxylate as a residue (intermediate 24).

To a stirred and cooled (0° C.) solution of 40 parts of ethyl 6-amino-3,4-dihydro-2H-1-benzopyran-2-carboxylate, 86 parts of pyridine and 234 parts of methylbenzene was added dropwise a solution of 20.6 parts of methanesulfonyl chloride in 135 parts of methylbenzene. Upon completion, stirring was continued overnight at room temperature. The reaction mixture was evaporated and the oily residue was taken up in water. The product was extracted with dichloromethane. The extract was dried, filtered and evaporated. The residue was purified by column chromatography over silica gel using a mixture of trichloromethane and methanol, saturated with ammonia, (95:5 by volume) as eluent. The pure fractions were collected and the eluent was evaporated. The residue was crystallized from a mixture of 210 parts of 2,2'-oxybispropane and 12 parts of acetonitrile, yielding 10.2 parts (18.9%) of ethyl 3,4-dihydro-6-[(methylsulfonyl)amino]-2H-1-benzopyran-2-carboxylate; mp. 111.1° C. (intermediate 25).

EXAMPLE 9

A mixture of 152 parts of 3,4-dihydro-2-methyl-4-oxo-2H-1-benzopyran-2-carboxylic acid, 18.4 parts of concentrate sulfuric acid and 2720 parts of ethanol was stirred overnight at reflux temperature. The reaction mixture was evaporated and the residue was taken up in a mixture of 1,1'-oxybisethane and a sodium hydroxide solution. The organic layer was separated, washed with water, dried, filtered and evaporated. The residue was purified by column chromatography over silica gel using trichloromethane as eluent. The pure fractions were collected and the eluent was evaporated, yielding 126 parts (72.7%) of ethyl 3,4-dihydro-2-methyl-4-oxo-2H-1-benzopyran-2-carboxylate as a residue (intermediate 26).

A mixture of 126 parts of ethyl 3,4-dihydro-2-methyl-4-oxo-2H-1-benzopyran-2-carboxylate and 560 parts of ethanol was hydrogenated at normal pressure and at room temperature with 5 parts of palladium-on-charcoal catalyst 10%. After the calculated amount of hydrogen was taken up, the catalyst was filtered off and the filtrate was evaporated. The residue was distilled, yielding 95.5 parts (80.3%) of ethyl 3,4-dihydro-2-methyl-2H-1-benzopyran-2-carboxylate; bp. 71°–73° C. at 0.5 mm. pressure (intermediate 27).

EXAMPLE 10

To a stirred mixture of 40 parts of ethyl 3,4-dihydro-6-hydroxy-2H-1-benzopyran-2-carboxylate and 360 parts of N,N-dimethylformamide were added portionwise 8.6 parts of a sodium hydride dispersion 50% (foaming). After stirring for 30 minutes, a solution of 21.7 parts of 3-bromo-1-propene in 18 parts of N,N-dimethylformamide was added dropwise. Upon completion, the whole was heated to about 70° C. and stirring was continued for 22 hours at 70° C. The reaction mixture was evaporated and the residue was taken up in water. The product was extracted with 1,1'-oxybisethane. The extract was washed with a sodium chloride solution 10%, dried, filtered and evaporated. The oily residue was purified by column chromatography over silica gel using trichloromethane as eluent. The pure fractions were collected and the eluent was evaporated, yielding 33.6 parts (70.2%) of ethyl 3,4-dihydro-6-(2-propenyloxy)-2H-1-benzopyran-2-carboxylate as a residue (intermediate 28).

EXAMPLE 11

To a stirred solution of 5.6 parts of ethyl 3,4-dihydro-6-hydroxy-2H-1-benzopyran-2-carboxylate in 90 parts of N,N-dimethylformamide were added portionwise 1.2 parts of a sodium hydride dispersion 50%. Upon completion, stirring was continued for 30 minutes. A solution of 3.1 parts of (chloromethyl)benzene in 18 parts of N,N-dimethylformamide was added dropwise. Upon completion, the whole was stirred for 22 hours at 70° C. The reaction mixture was evaporated. Water was added. The product was extracted with 1,1'-oxybisethane. The extract was washed with a sodium chloride solution 10%, dried, filtered and evaporated. The residue was purified by column chromatography over silica gel using trichloromethane as eluent. The pure fractions were collected and the eluent was evaporated, yielding 6 parts (76.9%) of ethyl 3,4-dihydro-6-(phenylmethoxy)-2H-1-benzopyran-2-carboxylate as a residue (intermediate 29).

EXAMPLE 12

A mixture of 20 parts of 3,4,7,8,9,10-hexahydro-2H-naphtho[1,2-b]pyran-2-carboxylic acid, 200 parts of ethanol and 4.6 parts of sulfuric acid was stirred and refluxed for 2 hours. The reaction mixture was evaporated. Water and a sodium hydroxide solution were added to the residue. The product was extracted with dichloromethane. The extract was washed with water, dried, filtered and evaporated, yielding 21 parts (100%) of ethyl 3,4,7,8,9,10-hexahydro-2H-naphtho[1,2-b]pyran-2-carboxylate as a residue (intermediate 30).

In a similar manner there was also prepared: ethyl 3,4-dihydro-2H-naphtho[1,2-b]pyran-2-carboxylate (intermediate 31).

EXAMPLE 13

65 Parts of (±)-3,4-dihydro-2H-1-benzopyran-2-carboxylic acid were taken up in 44 parts of (+)-α-methylbenzenemethanamine in ethanol. The precipitated product was set aside and the filtrate was evaporated. The residue was treated with a hydrochloric acid solution 10% and extracted with 1,1'-oxybisethane. The extract was dried, filtered and evaporated. The residue was dissolved in 120 parts of ethanol and this solution was treated with a solution of 27.6 parts of (−)-α-methylbenzenemethanamine in 80 parts of ethanol. The precipitated product was filtered off and crystallized three times from ethanol. The product was filtered off, taken up in water, treated with a hydrochloric acid solution 10% and extracted with 1,1'-oxybisethane. The extract was dried, filtered and evaporated, yielding 4.2 parts (6%) of (+)-3,4-dihydro-2H-1-benzopyran-2-carboxylic acid; mp. 82.8° C. (intermediate 32).

To a stirred solution of 65 parts of (±)-3,4-dihydro-2H-1-benzopyran-2-carboxylic acid in 160 parts of ethanol was added a solution of 44 parts of (+)-α-methylbenzenemethanamine in 80 parts of ethanol. The precipitated product was filtered off (the filtrate was set aside) and crystallized four times from ethanol. The product was filtered off, dissolved in water, treated with a hydrochloric acid solution 10% and extracted with 1,1'-oxybisethane. The extract was dried, filtered and evaporated, yielding 8.6 parts (13%) of (−)-3,4-dihydro-2H-1-benzopyran-2-carboxylic acid; mp. 82.5° C. (intermediate 33).

EXAMPLE 14

To a stirred solution of 72 parts of ethanedioyl dichloride in 650 parts of dichloromethane were added, during a period of 10 minutes, 83.5 parts of dimethyl sulfoxide at −60° C. and under nitrogen atmosphere. After stirring for 10 minutes, a solution of 97 parts of 3,4-dihydro-5,7-dimethyl-2H-1-benzopyran-2-methanol in 130 parts of dichloromethane was added during a 5 minutes period. The whole was stirred for 15 minutes and 242.9 parts of N,N-diethylethanamine were added. The reaction mixture was allowed to reach room temperature. It was poured into water. The product was extracted with dichloromethane. The extract was washed successively with water, a hydrochloric acid solution 10%, water, a sodium hydrogen carbonate solution 10% and water, dried, filtered and evaporated. The oily residue was crystallized from a small amount of petroleumether. The product was filtered off and dried, yielding 58 parts (72%) of 3,4-dihydro-5,7-dimethyl-2H-1-benzopyran-2-carboxaldehyde (intermediate 34).

Following the same procedure and using equivalent amounts of the appropriate starting materials, there were also prepared:

6-fluoro-3,4-dihydro-2H-1-benzopyran-2-carboxaldehyde (intermediate 35);
N-(2-formyl-3,4-dihydro-2H-1-benzopyran-6-yl)acetamide (intermediate 36);
3,4-dihydro-7-methyl-2H-1-benzopyran-2-carboxaldehyde (intermediate 37);
methyl 2-formyl-3,4-dihydro-2H-1-benzopyran-6-carboxylate (intermediate 38);
2-formyl-3,4-dihydro-2H-1-benzopyran-6-carbonitrile (intermediate 39);
3,4-dihydro-6-methoxy-2H-1-benzopyran-2-carboxaldehyde (intermediate 40); and
6-bromo-3,4-dihydro-2H-1-benzopyran-2-carboxaldehyde (intermediate 41).

EXAMPLE 15

To a stirred solution of 48 parts of ethyl 3,4-dihydro-6-(phenylmethoxy)-2H-1-benzopyran-2-carboxylate in 495 parts of methylbenzene were added dropwise 108 parts of a solution of [bis(2-methylpropyl)]aluminium hydride in methylbenzene at −80° C. Upon completion, stirring was continued for 30 minutes at −80° C. The reaction mixture was decomposed by the carefully addition of 24 parts of methanol. It was poured into 1000 parts of water and the whole was stirred for 15 minutes very carefully! The mixture was acidified with concentrate hydrochloric acid. After stirring for 5 minutes, the organic layer was separated, washed with water, dried, filtered and evaporated, yielding 39.8 parts (97%) of 3,4-dihydro-6-(phenylmethoxy)-2H-1-benzopyran-2-carboxaldehyde as a residue (intermediate 42).

In a similar manner there were also prepared:
3,4-dihydro-6-methyl-2H-1-benzopyran-2-carboxaldehyde (intermediate 43);
3,4,7,8,9,10-hexahydro-2H-naphtho[1,2-b]pyran-2-carboxaldehyde (intermediate 44);
3,4-dihydro-2H-naphtho[1,2-b]pyran-2-carboxaldehyde (intermediate 45);
3,4-dihydro-6-(2-propenyloxy)-2H-1-benzopyran-2-carboxaldehyde (intermediate 46); and
3,4-dihydro-2-methyl-2H-1-benzopyran-2-carboxaldehyde (intermediate 47);
N-(2-formyl-3,4-dihydro-2H-1-benzopyran-6-yl)methanesulfonamide (intermediate 48).

EXAMPLE 16

To a stirred solution of 12 parts of (+)-3,4-dihydro-2H-1-benzopyran-2-carboxylic acid in 270 parts of tetrahydrofuran were added 11 parts of 1,1'-carbonylbis[1H-imidazole]. After stirring for 1 hour at room temperature, the whole was cooled to −70° C. and 84 parts of a solution of bis(2-methylpropyl)aluminum hydride 1.5M in methylbenzene were added dropwise. Upon completion, stirring was continued for 20 minutes at −70° C. After the addition of 40 parts of methanol, the reaction mixture was poured onto water. The whole was acidified and the product was extracted with 1,1'-oxybisethane. The extract was washed with water, dried, filtered and evaporated. The residue was purified by filtration over silica gel using trichloromethane as eluent. The pure fractions were collected and the eluent was evaporated, yielding 9.50 parts (84%) of (+)-3,4-dihydro-2H-1-benzopyran-2-carboxaldehyde as a residue; $[\alpha]_D = +94.8°$ (c=1% in CH$_3$OH) (intermediate 49).

To a stirred solution of 8 parts of (−)-3,4-dihydro-2H-1-benzopyran-2-carboxylic acid in 225 parts of tetrahydrofuran were added 7.2 parts of 1,1'-carbonylbis[1H-imidazole]. After stirring for 1 hour at room temperature, the whole was cooled to −65° C. and 84 parts of a solution of bis(2-methylpropyl)aluminum hydride 1.5M in methylbenzene were added dropwise during a 10 minutes-period. Upon completion, stirring was continued for 15 minutes at −65° C. After the addition of 16 parts of methanol, the reaction mixture was poured onto water. The whole was acidified and the product was extracted with 1,1'-oxybisethane. The extract was washed with water, dried, filtered and evaporated. The residue was purified by filtration over silica gel using trichloromethane as eluent. The pure fractions were collected and the eluent was evaporated, yielding 6.6 parts (65%) of (−)-3,4-dihydro-2H-1-benzopyran-2-carboxaldehyde as a residue; $[\alpha]_D = -97.96°$ (c=1% in CH$_3$OH) (intermediate 50).

EXAMPLE 17

4.5 Parts of a sodium hydride dispersion 50% were washed three times with petroleumether under nitrogen atmosphere. Then there were added 150 parts of dimethyl sulfoxide. After stirring for 10 minutes, 18.3 parts of trimethylsulfoxonium iodide were added and the whole was further stirred for 20 minutes. Then there were added portionwise, during a 20 minutes-period, 8.6 parts of (+)-3,4-dihydro-2H-1-benzopyran-2-carboxaldehyde. Upon completion, stirring was continued for 2 hours at room temperature. The reaction mixture was poured onto water. The product was extracted with 1,1'-oxybisethane. The extract was washed with water, dried, filtered and evaporated. From the residue, the isomers were separated by column-chromatography over silica gel using methylbenzene as eluent. The pure fractions were collected and the eluent was evaporated. The first fraction (A-isomer) was collected and the eluent was evaporated, yielding 3.5 parts of (A+)-3,4-dihydro-2-oxiranyl-2H-1-benzopyran as a residue (intermediate 51). The second fraction (B-isomer), yield (B+)-3,4-dihydro-2-oxiranyl-2H-1-benzopyran.

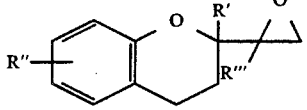

| No. | R' | R" | R'" | Isometric form |
|---|---|---|---|---|
| 52 | H | H | H | A⁻ |
| 53 | H | H | H | B+ |
| 54 | H | H | H | B⁻ |
| 55 | H | 6-F | H | A |
| 56 | H | 6-F | H | B |
| 57 | H | 6-CH₃ | H | A |
| 58 | H | 6-CH₃ | H | B |
| 59 | H | H | CH₃ | B |
| 60 | H | H | CH₃ | A |
| 61 | H | 6-CH₃—CO—NH | H | A |
| 62 | H | 6-CH₃—CO—NH | H | B |
| 63 | H | 7-CH₃ | H | A |
| 64 | H | 7-CH₃ | H | B |
| 65 | H | 6-CH₃—O—CO | H | A |
| 66 | H | 6-CH₃—O—CO | H | B |
| 67 | H | 6-CN | H | A |
| 68 | H | 6-CN | H | B |
| 69 | H | 6-CH₃O | H | A |
| 70 | H | 6-CH₃O | H | B |
| 71 | H | 6-C₆H₅—CH₂O | H | B |
| 72 | H | 6-Br | H | A |
| 73 | H | 6-C₆H₅—CH₂O | H | A |
| 74 | H | 6-Br | H | B |
| 75 | H | 6-CH₂=CH—CH₂O | H | A |
| 76 | H | 6-CH₂=CH—CH₂O | H | B |
| 77 | CH₃ | H | H | A |
| 78 | H | 6-CH₃—SO₂—NH | H | B |
| 79 | H | 6-CH₃—SO₂—NH | H | A |

In a similar manner there were also prepared:
(A)-3,4-dihydro-5,7-dimethyl-2-oxiranyl-2H-1-benzopyran; (intermediate 80)
(B)-3,4-dihydro-5,7-dimethyl-2oxiranyl-2H-1-benzopyran (intermediate 81);
(A)-3,4,7,8,9,10-hexahydro-2-oxiranyl-2H-naphtho[1,2-b]pyran (intermediate 82);
(B)-3,4,7,8,9,10-hexahydro-2-oxiranyl-2H-naphtho[1,2-b]pyran (intermediate 83)
(A)-3,4-dihydro-2-oxiranyl-2H-naphtho[1,2-b]pyran (intermediate 84); and
(B)-3,4-dihydro-2-oxiranyl-2H-naphtho[1,2-b]pyran (intermediate 85).

EXAMPLE 18

A mixture of 22 parts of 2,3-dihydro-2(2-methyl-1-propenyl)benzofuran, 29 parts of 3-chlorobenzenecarboperoxoic acid and 650 parts of dichloromethane was stirred over weekend at room temperature. The precipitate was filtered off and the filtrate was washed once with a hydrogen sulfite solution, twice with a sodium hydrogen carbonate solution and once with water, dried, filtered and evaporated. The residue was purified by column chromatography over silica gel using a mixture of trichloromethane and hexane (10:90 by volume) as eluent. The pure fractions were collected and the eluent was evaporated. The residue was further purified by column chromatography (HPLC) over silica gel using methylbenzene as eluent. The first fraction was collected and the eluent was evaporated, yielding 3.4 parts (13.1%) of (A)-2,3-dihydro-2-oxiranylbenzofuran as a residue (intermediate 86).

In a similar manner there were also prepared:
(B)-3,4-dihydro-2-oxiranyl-2H-1-benzopyran (intermediate 87); and
(A)-3,4-dihydro-2-oxiranyl-2H-1-benzopyran (intermediate 88).

EXAMPLE 19

A mixture of 2.6 parts of (A)-6-fluoro-3,4-dihydro-2-oxiranyl-2H-1-benzopyran, 4.3 parts of benzenemethanamine, 40 parts of absolute ethanol was stirred and refluxed overnight. The reacton mixture was evaporated. The only residue was crystallized from 2,2'-oxybispropane. The product was filtered off and dried, yielding 2.9 parts (72.5%) of (A)-6-fluoro-3,4-dihydro-α-[[(phenylmethyl)amino]methyl]-2H-1-benzopyran-2-methanol; mp. 121.8° C. (intermediate 89).

Following the same procedure and using equivalent amounts of the appropriate starting materials, there were also prepared:
(B)-3,4-dihydro-α-[[(phenylmethyl)amino]methyl]-2H-1-benzopyran-2-methanol; mp. 104.1° C. (intermediate 90);
(A)-3,4-dihydro-α-[[(phenylmethyl)amino]methyl]-2H-1-benzopyran-2-methanol; mp. 100.5° C. (intermediate 91);
(A+)-3,4-dihydro-α-[[(phenylmethyl)amino]methyl]-2H-1-benzopyran-2-methanol; $[α]_D = +83.80°$ (c=0.33% in methanol) (intermediate 92);
(A−)-3,4-dihydro-α-[[(phenylmethyl)amino]methyl]-2H-1-benzopyran-2-methanol; $[α]_D = -88.09°$ (c=1% in methanol) (intermediate 93);
(A)-3,4-dihydro-6-methyl-α-[[(phenylmethyl)amino]methyl]-2H-1-benzopyran-2-methanol; mp. 92.1° C. (intermediate 94);
(B)-3,4-dihydro-α-methyl-α-[[(phenylmethyl)amino]methyl]-2H-1-benzopyran-2-methanol (intermediate 95);
(A)-3,4-dihydro-7-methyl-α-[[(phenylmethyl)amino]methyl]-2H-1-benzopyran-2-methanol (intermediate 96);
(B+)-3,4-dihydro-α-[[(phenylmethyl)amino]methyl]-2H-1-benzopyran-2-methanol (intermediate 97);
methyl (A)-3,4-dihydro-2-[1-hydroxy-2-[(phenylmethyl)amino]ethyl]-2H-1-benzopyran-6-carboxylate; mp. 115° C. (intermediate 98); and
methyl (B)-3,4-dihydro-2-[1-hydroxy-2-[(phenylmethyl)amino]ethyl]-2H-1-benzopyran-6-carboxylate; mp. 130° C. (intermediate 99).

EXAMPLE 20

A mixture of 5 parts of (B)-3,4-dihydro-α-[[(phenylmethyl)amino]methyl]-2H-1-benzopyran-2-methanol and 160 parts of ethanol was hydrogenated at normal pressure and at room temperature with 0.2 parts palladium-on-charcoal catalyst 2%. After the calculated amount of hydrogen was taken up, the catalyst was filtered off and the filtrate was evaporated. The residue was crystallized from acetonitile, yielding 3.1 parts (B)-α-(aminomethyl)-3,4-dihydro-2H-1-benzopyran-2-methanol (89.1%) of; mp. 135° C. (intermediate 100).

In a similar manner there were also prepared:
(A)-α-(aminomethyl)-3,4-dihydro-2H-1-benzopyran-2-methanol (intermediate 101).

B. Preparation of Final compounds

EXAMPLE 21

A mixture of 7.7 parts of (A)-3,4-dihydro-2-oxiranyl-2H-1-benzopyran, 9.3 parts of benzenemethanamine and 160 parts of absolute ethanol was stirred and refluxed for 4 hours. The reaction mixture was evaporated. The residue was purified by column chromatography over silica gel using a mixture of trichloromethane and methanol (95:5 by volume) as eluent. The pure fractions were collected and the eluent was evaporated, yielding 1.8 parts (8%) of (A,A)-α,α'-[[(phenylmethyl)imino]bis(methylene)]bis[3,4-dihydro-2H-1-benzopyran-2-methanol] as an oily residue (compound 1).

Following the same procedure and using equivalent amounts of the appropriate starting materials, there were also prepared:

(B,B)-α,α'-[[(phenylmethyl)imino]bis(methylene)]-bis[3,4-dihydro-2H-1-benzopyran-2-methanol] (compound 2);

(A⁻A⁻)-α,α'-[[(phenylmethyl)imino]bis(methylene)]-bis[3,4-dihydro-2H-1-benzopyran-2-methanol] (compound 3);

(B⁻B⁻)-α,α'[[(phenylmethyl)imino]bis(methylene)]-bis[3,4-dihydro-2H-1-benzopyran-2-methanol] (compound 4);

(A,A)-α,α'-[[(phenylmethyl)imino]bis(methylene)]-bis[3,4-dihydro-6-methyl-2H-1-benzopyran-2-methanol] (compound 5);

(B,B)-α,α'-[[(phenylmethyl)imino]bis(methylene)]-bis[3,4-dihydro-6-methyl-2H-1-benzopyran-2-methanol] (compound 6);

(B,B)-α,α'-[[(phenylmethyl)imino]bismethylene]-bis[3,4,7,8,9,10-hexahydro-2H-naphtho[1,2-b]pyran-2-methanol] (compound 7);

(A,A)-α,α'-[[(phenylmethyl)imino]bismethylene]-bis[2,3-dihydro-2-benzofuranmethanol] (compound 8);

(B+B+)-α,α'[[(phenylmethyl)imino]bismethylene]-bis[3,4-dihydro-2H-1-benzopyran-2-methanol] (compound 9);

(B,B)-α,α'-[iminobismethylene]bis[6-bromo-3,4-dihydro-2H-1-benzopyran-2-methanol]; mp. 195.4° C. (compound 10);

A,A-α,α'-[[(phenylmethyl)imino]bismethylene]bis[3,4-dihydro-2-methyl-2H-1-benzopyran-2-methanol]; mp. 123.5° C. (compound 11); and (A,A)-α,α'-[[(phenylmethyl)imino]bismethylene]-bis[3,4-dihydro-6-(phenyl-methoxy)-2H-1-benzopyran-2-methanol] (compound 12).

EXAMPLE 22

A mixture of 1.4 parts of (A)-3,4-dihydro-2-oxiranyl-2H-1-benzopyran, 2.2 parts of (B)-3,4-dihydro-α-[[(phenylmethyl)amino]methyl]-2H-1-benzopyran-2-methanol and 40 parts of ethanol was stirred and refluxed for 6 hours. The reaction mixture was evaporated and the oily residue was purified by column chromatography over silica gel using a mixture of trichloromethane and methanol (95:5 by volume) as eluent. The oily residue was converted into the ethanedioate salt in 2-propanol. The salt was filtered off and crystallized from ethanol, yielding, after drying, 1.4 parts of (A,B)-α,α'-[[(phenylmethyl)-imino]bis(methylene)]bis[3,4-dihydro-2H-1-benzopyran-2methanol]ethanedioate (1:1); mp. 173.7° C. (compound 13).

Following the same procedure and using equivalent amounts of the appropriate starting materials, there were also prepared:

[Structure: base with R¹², R¹⁶ substituents on benzopyran rings, with OH, CH₂, N-CH₂, HO, C, R⁴, R⁵, and CH₂-phenyl]

| Comp. no. | R⁴ | R⁵ | R¹² | R¹⁶ | Isomeric form |
|---|---|---|---|---|---|
| 14 | H | H | H | H | A⁺B⁺ |
| 15 | H | H | H | H | A⁺B⁻ |
| 16 | H | H | H | H | A⁻B⁺ |
| 17 | H | H | H | H | A⁻B⁻ |
| 18 | H | H | F | F | AB |
| 19 | H | H | CH₃ | CH₃ | AB |
| 20 | CH₃ | CH₃ | H | H | AB |
| 21 | H | H | F | F | AA |
| 22 | H | H | H | H | A⁺A⁺ |
| 23 | H | H | H | H | A⁺A⁻ |
| 24 | H | H | CH₃ | H | AB |
| 25 | H | H | CH₃ | H | AA |
| 26 | H | H | F | H | BA |
| 27 | CH₃ | H | H | H | AA |
| 28 | H | H | CH₃ | H | BA |
| 29 | H | H | CH₃CONH | H | AB |
| 30 | H | H | CH₃CONH | H | BA |
| 31 | H | H | CH₃CONH | H | AA |

Following the same procedure and using equivalent amounts of the appropriate starting materials, there were also prepared:

[Structure: base with R¹⁰, R¹¹, R¹², R¹³ on left benzopyran and R¹⁵ on right benzopyran, with R⁶, OH, C, CH₂, N, R¹, CH₂, CH, HO, R⁴]

| Comp. no. | R¹ | R⁶ | R¹⁰ | R¹¹ | R¹² | R¹³ | R¹⁵ | Isomeric form | mp. °C. |
|---|---|---|---|---|---|---|---|---|---|
| 32 | C₆H₅CH₂ | H | H | CH₃ | H | H | H | AB | — |
| 33 | C₆H₅CH₂ | H | H | CH₃ | H | H | H | AA | — |
| 34 | C₆H₅CH₂ | H | H | CH₃ | H | H | H | BA | — |
| 35 | C₆H₅CH₂ | H | H | CH₃ | H | H | CH₃ | AB | — |
| 36 | C₆H₅CH₂ | H | H | CH₃ | H | H | CH₃ | BB | — |
| 37 | C₆H₅CH₂ | H | H | CH₃ | H | H | CH₃ | AA | — |
| 38 | C₆H₅CH₂ | H | H | CH₃ | H | CH₃ | H | AA | — |
| 39 | C₆H₅CH₂ | H | H | CH₃ | H | CH₃ | H | AB | — |

-continued

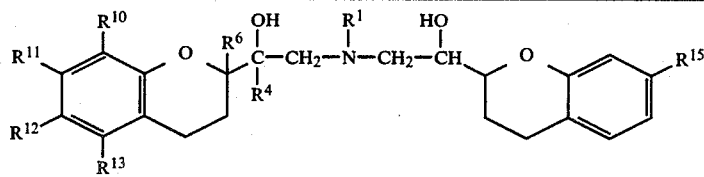

base

| Comp. no. | $R^1$ | $R^6$ | $R^{10}$ | $R^{11}$ | $R^{12}$ | $R^{13}$ | $R^{15}$ | Isomeric form | mp. °C. |
|---|---|---|---|---|---|---|---|---|---|
| 40 | $C_6H_5CH_2$ | H | H | $CH_3$ | H | $CH_3$ | H | BB | — |
| 41 | $C_6H_5CH_2$ | H | H | $CH_3$ | H | $CH_3$ | H | BA | — |
| 42 | $C_6H_5CH_2$ | H | H | H | H | H | H | $B^-B^+$ | — |
| 43 | $C_6H_5CH_2$ | H | $-(CH_2)_4-$ | | H | H | H | AA | — |
| 44 | $C_6H_5CH_2$ | H | $-(CH_2)_4-$ | | H | H | H | BA | — |
| 45 | $C_6H_5CH_2$ | H | $-(CH_2)_4-$ | | H | H | H | AB | — |
| 46 | $C_6H_5CH_2$ | H | $-(CH_2)_4-$ | | H | H | H | BB | — |
| 47 | $C_6H_5CH_2$ | H | H | H | $CH_3O-C(O)$ | H | H | AA | — |
| 48 | $C_6H_5CH_2$ | H | H | H | $CH_3O-C(O)$ | H | H | AB | — |
| 49 | $C_6H_5CH_2$ | H | H | H | $CH_3O-C(O)$ | H | H | BA | — |
| 50 | $C_6H_5CH_2$ | H | H | H | $CH_3O-C(O)$ | H | H | BB | — |
| 51 | H | H | H | H | NC | H | H | AB | 154.0 |
| 52 | H | H | H | H | NC | H | H | AA | 160.5 |
| 53 | H | H | H | H | NC | H | H | BA | 135.5 |
| 54 | H | H | H | H | NC | H | H | BB | 145.1 |
| 55 | $C_6H_5CH_2$ | H | $-CH=CH-CH=CH-$ | | H | H | H | AA | — |
| 56 | $C_6H_5CH_2$ | H | $-CH=CH-CH=CH-$ | | H | H | H | AB | — |
| 57 | $C_6H_5CH_2$ | H | $-CH=CH-CH=CH-$ | | H | H | H | BA | — |
| 58 | $C_6H_5CH_2$ | H | $-CH=CH-CH=CH-$ | | H | H | H | BB | — |
| 59 | $C_6H_5CH_2$ | H | H | H | $CH_3O$ | H | H | AA | — |
| 60 | $C_6H_5CH_2$ | H | H | H | $CH_3O$ | H | H | AB | — |
| 61 | $C_6H_5CH_2$ | H | H | H | $CH_3O$ | H | H | BA | — |
| 62 | $C_6H_5CH_2$ | H | H | H | $CH_3O$ | H | H | BB | — |
| 63* | H | H | H | H | Br | H | H | AA | 196.0 |
| 64 | $C_6H_5CH_2$ | H | H | H | $C_6H_5CH_2O$ | H | H | AA | — |
| 65 | H | H | H | H | $CH_2=CH-CH_2O$ | H | H | AB | 123.8 |
| 66 | H | H | H | H | $CH_2=CH-CH_2O$ | H | H | BA | 123.8 |
| 67 | H | H | H | H | $CH_2=CH-CH_2O$ | H | H | AA | 128.1 |
| 68 | $C_6H_5CH_2$ | H | H | H | $C_6H_5CH_2O$ | H | H | AB | — |
| 69 | $C_6H_5CH_2$ | H | H | H | $C_6H_5CH_2O$ | H | H | BA | — |
| 70 | $C_6H_5CH_2$ | $CH_3$ | H | H | H | H | H | AA | — |
| 71 | $C_6H_5CH_2$ | H | H | H | $CH_3S(O)_2-NH$ | H | H | BA | — |
| 72 | $C_6H_5CH_2$ | H | H | H | $CH_3S(O)_2-NH$ | H | H | AA | — |
| 73 | $C_6H_5CH_2$ | $CH_3$ | H | H | H | H | H | AB | — |

*ethanedioate salt (1:1)

EXAMPLE 23

A mixture of 3 parts of $(A^+A^+)$-$\alpha,\alpha'$-[[(phenylmethyl)imino]bis(methylene)]bis[3,4-dihydro-2H-1-benzopyran-2-methanol] and 120 parts of methanol was hydrogenated at normal pressure and at room temperature with 2 parts of palladium-on-charcoal catalyst 10%. After the calculated amount of hydrogen was taken up, the catalyst was filtered off and the filtrate was evaporated. The residue was taken up in dichloromethane. The organic phase was washed with a 10% sodium hydroxide solution and with water, dried, filtered and evaporated. The residue was dried in vacuo at 80° C., yielding 1.2 parts (19%) of $(A^+A^+)$-$\alpha,\alpha'$-[iminobis(methylene)]bis[3,4-dihydro-2H-1-benzopyran-2-methanol]; mp. 130.8° C.; $[\alpha]_{589} = +121.50°$ (c=1% $CH_3OH$) (compound 74).

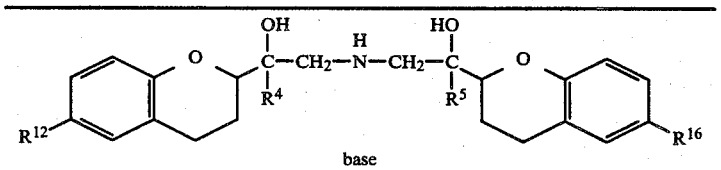

base

| Comp. no. | $R^4$ | $R^5$ | $R^{12}$ | $R^{16}$ | Isomeric form | mp. in °C. | $[\alpha]_D$ (c = 1% in methanol) |
|---|---|---|---|---|---|---|---|
| 75 | H | H | H | H | BB | 156.8 | — |
| 76 | H | H | H | H | AB | 148.1 | — |
| 77 | H | H | H | H | AA | 146.1 | — |
| 78 | H | H | H | H | $A^+B^+$ | — | +12.5761° |
| 79* | H | H | H | H | $A^+B^+$ | 162.5 | — |
| 80 | H | H | H | H | $A^+B^-$ | 165.0 | — |
| 81* | H | H | H | H | $A^+B^-$ | 162.8 | — |
| 82* | H | H | H | H | $A^-B^+$ | 160.3 | — |

-continued

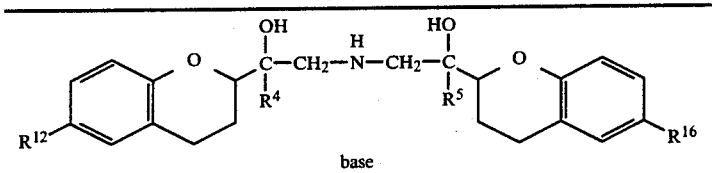

base

| Comp. no. | $R^4$ | $R^5$ | $R^{12}$ | $R^{16}$ | Isomeric form | mp. in °C. | $[\alpha]_D$ (c = 1% in methanol) |
|---|---|---|---|---|---|---|---|
| 83* | H | H | H | H | A⁻B⁻ | 163.4 | — |
| 84 | H | H | F | F | AB | 140.7 | — |
| 85 | H | H | CH₃ | CH₃ | AB | 139.8 | — |
| 86 | CH₃ | CH₃ | H | H | AB | 143.3 | — |
| 87 | H | H | F | F | AA | 139.4 | — |
| 88 | H | H | H | H | A⁺A⁻ | 159.0 | −4.5963° |
| 89 | H | H | CH₃ | H | AB | 143.6 | — |
| 90 | H | H | CH₃ | H | AA | 141.8 | — |
| 91 | H | H | F | H | BA | 138.2 | — |
| 92* | CH₃ | H | H | H | AA | 176.5 | — |
| 93 | H | H | CH₃ | H | BA | 146.9 | — |
| 94 | H | H | CH₃CONH | H | AB | 175.5 | — |
| 95 | H | H | CH₃CONH | H | BA | 167.4 | — |
| 96 | H | H | CH₃CONH | H | AA | 172.1 | — |

*ethanedioate salt (1:1)

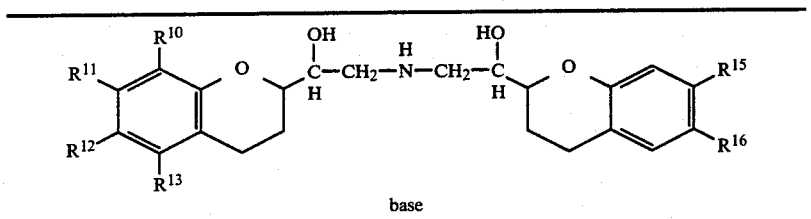

base

| Comp. no. | $R^{10}$ | $R^{11}$ | $R^{12}$ | $R^{13}$ | $R^{15}$ | $R^{16}$ | Isomeric form | mp. in °C. |
|---|---|---|---|---|---|---|---|---|
| 97 | H | CH₃ | H | H | H | H | AB | 161.1 |
| 98 | H | CH₃ | H | H | H | H | AA | 153.7 |
| 99 | H | CH₃ | H | H | H | H | BA | 152.7 |
| 100 | H | CH₃ | H | H | CH₃ | H | AB | 168.3 |
| 101 | H | CH₃ | H | H | CH₃ | H | BB | 177.3 |
| 102 | H | CH₃ | H | H | CH₃ | H | AA | 168.3 |
| 103 | H | CH₃ | H | CH₃ | H | H | AA | 149.9 |
| 104 | H | CH₃ | H | CH₃ | H | H | AB | 165.8 |
| 105 | H | CH₃ | H | CH₃ | H | H | BB | 158.5 |
| 106 | H | CH₃ | H | CH₃ | H | H | BA | 166.3 |
| 107 | H | H | H | H | H | H | A⁻A⁻ | 140.7 |
| 108 | H | H | H | H | H | H | B⁻B⁺ | 173.0 |
| 109 | H | H | H | H | H | H | B⁻B⁻ | 161.5 |
| 110 | —(CH₂)₄— | | H | H | H | H | AA | 148.7 |
| 111 | —(CH₂)₄— | | H | H | H | H | BA | 152.7 |
| 112** | H | H | CH₃ | H | H | CH₃ | AA | 229.6 |
| 113** | H | H | CH₃ | H | H | CH₃ | BB | 224.5 |
| 114 | —(CH₂)₄— | | H | H | —(CH₂)₄— | | BB | 180.2 |
| 115 | —(CH₂)₄— | | H | H | H | H | AB | 152.5 |
| 116 | —(CH₂)₄— | | H | H | H | H | BB | 121.7 |
| 117 | H | H | CH₃OC(O) | H | H | H | AA | 123.9 |
| 118 | H | H | CH₃OC(O) | H | H | H | AB | 151.4 |
| 119 | H | H | CH₃OC(O) | H | H | H | BA | 145.2 |
| 120 | H | H | CH₃OC(O) | H | H | H | BB | 148.5 |
| 121 | —CH=CH—CH=CH— | | H | H | H | H | AA | 142.9 |
| 122 | —CH=CH—CH=CH— | | H | H | H | H | AB | 145.5 |
| 123 | —CH=CH—CH=CH— | | H | H | H | H | BA | 156.8 |
| 124 | —CH=CH—CH=CH— | | H | H | H | H | BB | 147.8 |
| 125 | H | H | CH₃O | H | H | H | AA | 135.5 |
| 126 | H | H | CH₃O | H | H | H | AB | 133.2 |
| 127 | H | H | CH₃O | H | H | H | BA | 128.2 |
| 128 | H | H | CH₃O | H | H | H | BB | 133.9 |
| 129 | H | H | H | H | H | H | B⁺B⁺ | 165.5 |
| 130** | H | H | HO | H | H | H | A⁺A⁺ | 238.7 |
| 131* | H | H | HO | H | H | H | AB | 169.0 |
| 132*** | H | H | HO | H | H | H | BA | 201.8 |
| 133 | H | H | HO | H | H | HO | AA | 145.6 |
| 134 | H | H | CH₃S(O)₂NH | H | H | H | BA | 138.6 |

-continued

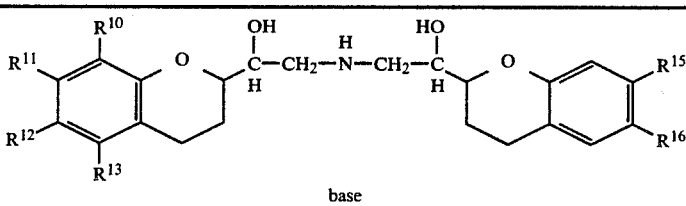

base

| Comp. no. | R10 | R11 | R12 | R13 | R15 | R16 | Isomeric form | mp. in °C. |
|---|---|---|---|---|---|---|---|---|
| 135 | H | H | CH$_3$S(O)$_2$NH | H | H | H | AA | 175.7 |

*ethanedioate salt (1:1)
**hydrochloride salt
***ethanedioate salt (1:1) monohydrate.

In a similar manner there were also prepared:
(A,A)-α,α-(iminobismethylene)bis[2,3-dihydro-2-benzofuranmethanol]; mp. 154.6° C. (compound 136);
(A,A)-α-[[acetyl[2-(3,4-dihydro-2H-1-benzopyran-2-yl)-2-hydroxyethyl]amino]-methyl]-3,4-dihydro-2H-1-benzopyran-2-methanol acetate (ester); mp. 152.9° C. (compound 137);
(A,A)-α-[[[2-(3,4-dihydro-2H-1-benzopyran-2-yl)-2-hydroxyethyl]amino]methyl]-3,4-dihydro-2H-1-benzopyran-2-methanol ethanedioate (1:1); mp. 178.8° C. (compound 138);
(A,A)-α,α'-(iminobismethylene)bis[3,4-dihydro-2-methyl-2H-1-benzopyran-2-methanol]hydrochloride. monohydrate; mp. 134.0° C. (compound 139); and
(A,B)-α-[[[2-(3,4-dihydro-2H-1-benzopyran-2-yl)-2-hydroxyethyl]amino]methyl]-3,4-dihydro-2-methyl-2H-1-benzopyran-2-methanol ethanedioate (1:1). monohydrate; mp. 166.1° C. (compound 140).

EXAMPLE 24

To a stirred mixture of 7.9 parts of (A,A)-α,α'-[[(phenylmethyl)imino]bis(methylene)]bis[3,4-dihydro-2H-1-benzopyran-2-methanol], 5.8 parts of pyridine and 157.5 parts of methylbenzene was added dropwise a solution of 5.7 parts of acetyl chloride in 54 parts of methylbenzene. Upon completion, stirring was continued for 4 hours at reflux temperature. After cooling to room temperature, the whole was washed with water. The organic layer was dried, filtered and evaporated. The residue was purified by column chromatography (HPLC) over silica gel using a mixture of dichloromethane and hexane (60:40 by volume) as eluent. The first fraction was collected and the eluent was evaporated, yielding 3.4 parts (36.7%) of (A,A)-α,α'-[[-(phenylmethyl)imino]bismethylene]bis[3,4-dihydro-2H-1-benzopyran-2-methanol]diacetate(ester) as a residue (compound 141).

EXAMPLE 25

To a stirred solution of 1 part of (A+A+)-α,α'-[iminobis(methylene)]bis[3,4-dihydro-2H-1-benzopyran-2-methanol] in 16 parts of 2-propanol were added dropwise 8 parts of 2-propanol saturated with hydrogen bromide. The product was filtered off and crystallized from 2-propanol. The product was filtered off and dried, yielding 0.8 parts of (A+A+)-α,α'-[iminobis(methylene)]bis[3,4-dihydro-2H-1-benzopyran-2-methanol]hydrobromide; mp. 236.5° C.; [α]$_{589}$ = +114.53° (c=1% CH$_3$OH) (compound 142).

In a similar manner there was also prepared:
(A+A+)-α,α'-[iminobis(methylene)]bis[3,4-dihydro-2H-1-benzopyran-2-methanol]hydrochloride; mp. 219.4° C. [α]$_{589}$ = +125.44° (c=1% CH$_3$OH) (compound 143).

EXAMPLE 26

The useful β-adrenergic receptor blocking activities of the compounds (I) are illustrated in vitro using the Guinea-pig right atrium test and the Guinea-pig tracheal ring test which are described hereafter.

1. Guinea-pig right atrium (β$_1$)

Spontaneously beating right atria were dissected from guinea-pigs (400±50 g). A triangular strip of atrium, including the sinoatrial node was excised together with the anterior vena cava.

The vena was fixed to a glass muscle holder and the opposite atrial muscle was connected to a Grass isometric transducer. Atria were suspended at optimal preload in a 100 ml Krebs-Henseleit solution, containing 2 g/l glucose, at 37.5° C. and aerated with 95% O$_2$ and 5% CO$_2$. Heart rate and contractile force were recorded by means of a Grass FT03C isometric transducer. Output signals amplified by an isometric transducer amplifier (J.S.I.) via a cardiotachometer (J.S.I.) were recorded on Honeywell XYY' recorder.

After a stabilisation period of 45 min. isoprenaline was infused in linearly increased doses for a period of 7 min. This produced a dose related increase in heart rate (a). After washing out isoprenaline a stabilisation period of 15 min. was allowed. A drug was then added to the bath fluid for 30 min. During this incubation period possible direct chronotropic and inotropic effects of the drug were determined. Following this, a second dose-response curve for isoprenaline was produced by infusion during 10 minutes (b). The slope of the increase in rate was graphically estimated for each period of isoprenaline addition and the ratio b/a was calculated. Based on solvent experiments a ratio of less than 0.70 was considered as the criterion of inhibitory activity. ED$_{50}$-values were estimated graphically.

2. Guinea-pig tracheal ring (β$_2$)

The trachea was dissected from guinea-pigs (400±50 g). Four rings, approximately 8 mm. in width, were then cut from each trachea. Cartilaginous parts of the tracheal ring were mounted horizontally between two metal rods, one of which was attached to a glass organholder, the other rod being connected to a Grass isometric transducer. Using such a technique the tracheal smooth muscle is suspended optimally i.e. midway between the cartilaginous parts. The prepared rings were suspended in a 100 ml organ chamber filled with Tyrode solution, maintained at 35° C. and aerated with 95% $O_2$ and 5% $CO_2$. The preparation was maintained at tension of 1.5 g throughout the experiment. Tension changes recorded were thus an expression of contraction or relaxation. After a stabilisation period of 30 min. contraction was induced by adding methacholine (1 μg/ml) to the bath for a 10 min. period. Addition of isoprenaline (0.08 μg/ml) for 4 min. in the presence of methacholine induced a relaxation of the tracheal ring. This procedure was repeated twice before adding the drug (t-33'; t-19') and once 30 min. after addition of the drug. During the incubation period any direct effects of the drug were measured. A 50% inhibition of the agonist-induced response was used as the criterion of effectiveness and $ED_{50}$ values (with fiducial limits) were determined by probit analysis.

The ratio of the $ED_{50}$-values obtained in respectively the tracheal ring test ($\beta_2$) and in the right atrium test ($\beta_1$) may be considered as an index of the cardioselectivity of the test drug. Typical results obtained in the above experiments with a number of the compounds of formula (I) are given in the following table I which is only intended to illustrate and not to limit the scope of the invention.

TABLE I

| Comp. No. | $ED_{50}$ value in mg/l on guinea pig atrium ($\beta_1$) | $ED_{50}$ value in mg/l on guinea pig trachea ($\beta_2$) | $\beta_2/\beta_1$ |
|---|---|---|---|
| 75 | 0.0013 | 2.8 | 2,154 |
| 76 | 0.00085 | 2.2 | 2,614 |
| 77 | 0.00054 | 2.2 | 4,074 |
| 79 | 0.00019 | 2.5 | 13,157 |
| 81 | 0.00016 | 0.63 | 3,938 |
| 82 | 0.0025 | >2.5 | >1,000 |
| 83 | 0.00046 | >2.5 | >5,435 |
| 84 | 0.00063 | >10 | >15,873 |
| 85 | 0.00023 | 1.3 | 5,652 |
| 86 | 0.0012 | 5.0 | 4,166 |
| 87 | 0.0025 | >10 | >4,000 |
| 74 | 0.00024 | 3.0 | 12,500 |
| 88 | 0.0025 | ≧10 | — |
| 89 | 0.00043 | 8.9 | 20,698 |
| 90 | 0.0004 | ≧10 | ≧25,000 |
| 91 | 0.0008 | 5.0 | 6,250 |
| 92 | 0.0004 | 5.0 | 12,500 |
| 93 | 0.00016 | 2.2 | 13,750 |
| 94 | ≧0.0025 | — | — |
| 95 | 0.00031 | 0.04 | 129 |
| 96 | 0.0013 | 0.14 | 108 |
| 97 | 0.00071 | 5.0 | 7,042 |
| 98 | 0.0025 | 6.0 | 2,400 |
| 99 | 0.00063 | ≧10 | ≧15,873 |
| 103 | 0.0025 | >10 | >4000 |
| 104 | 0.0013 | >2.5 | >1923 |
| 106 | 0.0025 | >2.5 | >1000 |
| 110 | 0.0025 | — | — |
| 113 | 0.0025 | — | — |
| 115 | 0.0025 | — | — |
| 51 | 0.0025 | >0.63 | >252 |
| 63 | <0.04 | — | — |
| 10 | 0.04 | — | — |
| 130 | 0.00031 | 0.31 | 1000 |
| 133 | 0.00063 | — | — |
| 138 | 0.01 | >10 | >1000 |
| 135 | 0.063 | — | — |
| 140 | ≦0.0025 | — | — |

EXAMPLE 27

The following formulations exemplify compositions typical for the normalization of irregular cardial rhythms in dosage unit form suitable for systemic administration to animal and human subjects in accordance with the instant invention.

Oral drops: The following formulation provides 50 liters of an oral-drop solution comprising 10 milligrams of active ingredient (A.I.) per milliliter.

| A.I. | 500 grams |
|---|---|
| 2-hydroxypropanoic acid | 0.5 liter |
| Sodium saccharin | 1750 grams |
| Cocoa flavor | 2.5 liters |
| Purified water | 2.5 liters |
| Polyethylene glycol q.s. ad | 50 liters |

The A.I. was dissolved in the 2-hydroxypropanoic acid and 1.5 liters of the polyethylene glycol at 60°–80° C. After cooling to 30°–40° C. there were added 35 liters of polyethylene glycol and the mixture was stirred well. Then there was added a solution of the sodium saccharin in 2.5 liters of purified water and while stirring there were added the cocoa flavor and polyethylene glycol q.s. ad volume. The resulting solution was filled into suitable containers.

Injectable solution: The following formulation provides 20 liters of a parenteral solution comprising 2 milligrams of active ingredient per milliliter.

| A.I. | 40 grams |
|---|---|
| 2,3-dihydroxybutanedioic acid | 20 grams |
| methyl 4-hydroxybenzoate | 36 grams |
| propyl 4-hydroxybenzoate | 4 grams |
| water for injection q.s. ad | 20 liters. |

The methyl and propyl 4-hydroxybenzoates were dissolved in about 10 liters of boiling water for injection. After cooling to about 50° C. there were added while stirring the 2,3-dihydroxybutanedioic acid and thereafter the A.I.. The solution was cooled to room temperature and supplemented with water for injection q.s. ad volume. The solution was sterilized by filtration (U.S.P. XVII p. 811) and filled in sterile containers.

Oral solution: The following formulation provides 20 liters of an oral solution comprising 5 milligrams of active ingredient per teaspoonful (5 milliliters).

| A.I. | 20 grams |
|---|---|
| 2,3-dihydroxybutanedioic acid | 10 grams |
| Sodium saccharin | 40 grams |
| 1,2,3-propanetriol | 12 liters |
| Sorbitol 70% solution | 3 liters |
| Methyl 4-hydroxybenzoate | 9 grams |
| Propyl 4-hydroxybenzoate | 1 gram |
| Raspberry essence | 2 milliliters |
| Gooseberry essence | 2 milliliters |
| Purified water q.s. ad | 20 liters. |

The methyl and propyl 4-hydroxybenzoates were dissolved in 4 liters of boiling purified water. In 3 liters of this solution were dissolved first the 2,3-dihydroxybutanedioic acid and thereafter the A.I.. The latter solution was combined with the remaining part of the former solution and the 1,2,3-propanetriol and the sorbitol solution were added thereto. The sodium saccharin was dissolved in 0.5 liters of water and the raspberry and gooseberry essences were added. The latter solution was combined with the former, water was added q.s. ad volume and the resulting solution was filled in suitable containers.

Film-coated tablets: 10,000 Compressed tablets, each containing 10 milligrams of active ingredient, were prepared from the following formulation:

| Tablet core: | |
|---|---|
| A.I. | 100 grams |
| Lactose | 570 grams |
| Starch | 200 grams |
| Polyvinylpyrrolidone (Kollidon K90) | 10 grams |
| Microcrystalline cellulose (Avicel) | 100 grams |
| Sodium dodecyl sulfate | 5 grams |
| Hydrogenated vegetable oil (Sterotex) | 15 grams |
| Coating: | |
| Methyl cellulose (Methocel 60 HG) | 10 grams |
| Ethyl cellulose (Ethocel 22 cps) | 5 grams |
| 1,2,3-propanetriol | 2.5 milliliters |
| Polyethylene glycol 6000 | 10 grams |
| Concentrated colour suspension (Opaspray K-1-2109) | 30 milliliters |
| Polyvinylpyrrolidone (Povidone) | 5 grams |
| Magnesium octadecanoate | 2.5 grams |

Preparation of tablet core:

A mixture of the A.I., the lactose and the starch was mixed well and thereafter humidified with a solution of the sodium dodecyl sulfate and the polyvinylpyrrolidone in about 200 milliliters of water. The wet powder was sieved, dried and sieved again. Then there was added the microcrystalline cellulose and the hydrogenated vegetable oil. The whole was mixed well and compressed into tablets.

Coating:

To a solution of the methyl cellulose in 75 milliliters of denaturated ethanol there was added a solution of the ethyl cellulose in 150 milliliters of dichloromethane. Then there were added 75 milliliters of dichloromethane and 1,2,3-propanetriol. The polyethylene glycol was molten and dissolved in 75 milliliters of dichloromethane. The latter solution was added to the former and then there were added the magnesium octadecanoate, the polyvinylpyrrolidone and the concentrated colour suspension and the whole was homogenized.

The tablet cores were coated with the thus obtained mixture in a coating apparatus.

Suppositories: Hundred suppositories each containing 3 milligrams active ingredient were prepared from the following formulations:

| A.I. | 0.3 grams |
|---|---|
| 2,3-dihydroxybutanedioic acid | 3 grams |
| Polyethylene glycol 400 | 25 milliliters |
| Surfactant (Span) | 12 grams |
| Triglycerides (Witepsol 555) q.s. ad | 300 grams. |

The A.I. was dissolved in a solution of the 2,3-dihydroxybutanedioic acid in polyethylene glycol 400. The surfactant and the triglycerides were molten together. The latter mixture was mixed well with the former solution. The thus obtained mixture was poured onto moulds at a temperature of 37°-38° C. to form the suppositories.

What we claim is:

1. A chemical compound having the formula

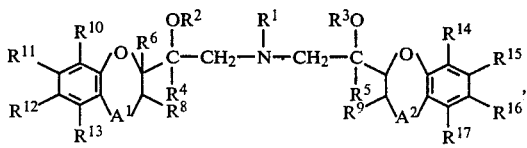

(I)

a pharmaceutically acceptable acid addition salt or a stereochemically isomeric form thereof, wherein $R^1$ is hydrogen, $C_{1-6}$ alkyl, aryl, aryl-$C_{1-6}$ alkyl, $C_{1-12}$ alkylcarbonyl or arylcarbonyl;

$R^2$ and $R^3$ are each independently hydrogen, $C_{1-12}$ alkylcarbonyl or arylcarbonyl;

$R^4$, $R^5$, $R^6$ and $R^7$ are each independently hydrogen or $C_{1-6}$ alkyl;

$A^1$ and $A^2$ are each independently a direct bond, or $CH_2$;

$R^8$ and $R^9$ are hydrogen; and $R^{10}$, $R^{11}$, $R^{12}$, $R^{13}$, $R^{14}$, $R^{15}$, $R^{16}$ and $R^{17}$ are each independently hydrogen, halo, $C_{1-6}$ alkyl, $C_{2-6}$ alkenyl, $C_{2-6}$ alkynyl, $C_{1-6}$ alkyloxy, $C_{2-6}$ alkenylmethoxy, $C_{1-6}$ alkylthio, trifluoromethyl, hydroxy, amino, mono or di($C_{1-6}$ alkyl)amino, arylamino, (aryl $C_{1-6}$ alkyl)amino, cyano, nitro, aryl, aryloxy, aryl $C_{1-6}$ alkyloxy, $C_{1-6}$ alkyloxy-$C_{1-6}$ alkyl or a radical of formula

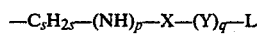

(a)

said s being 0 or an integer of from 1 to 6 inclusive;

said p and q being independently 0 or the integer 1;

said X being $>C=O$; $>C=S$; or $-S(=O)_2-$;

said Y being NH or O; and said L being hydrogen, $C_{1-6}$ alkyl, aryl or aryl-$C_{1-6}$ alkyl; or two vicinal radicals of $R^{10}$, $R^{11}$, $R^{12}$ and $R^{13}$ and of $R^{14}$, $R^{15}$, $R^{16}$ and $R^{17}$ may complete a phenyl-, cyclohexene dioxanyl- or dioxolanyl ring provided that L is other than hydrogen when X is $-S(=O)_2-$;

provided that not more than two radicals of $R^{10}$, $R^{11}$, $R^{12}$ and $R^{13}$ or of $R^{14}$, $R^{15}$, $R^{16}$ and $R^{17}$ are amino, mono- or di($C_{1-6}$ alkyl)amino, arylamino, (aryl-$C_{1-6}$ alkyl)amino, nitro, aryl, aryloxy or a radical of formula (a); p1 wherein aryl as used in the foregoing definitions is phenyl optionally substituted with up to three substituents each independently selected from the group consisting of halo, lower alkyl, lower alkyloxy, loweralkylthio, trifluoromethyl, nitro and amino.

2. α, α′-[iminobis(methylene)]bis[3,4-dihydro-2H-1-benzopyran-2-methanol], a pharmaceutically acceptable acid addition salt or a stereochemically isomeric form thereof.

3. A pharmaceutical composition for the treatment and/or prevention of disorders of the coronary vascular system in patients suffering from same, contaning a pharmaceutically acceptable inert carrier and a pharmaceutically effective amount of a compound having the formula

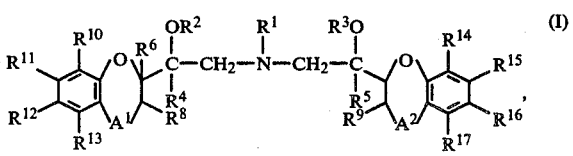

(I)

a pharmaceutically acceptable acid addition salt or a stereochemically isomeric form thereof, wherein $R^1$ is hydrogen, $C_{1-6}$ alkyl, aryl, aryl-$C_{1-6}$ alkyl, $C_{1-12}$ alkylcarbonyl or arylcarbonyl;

$R^2$ and $R^3$ are each independently hydrogen, $C_{1-12}$ alkylcarbonyl or arylcarbonyl;

$R^4$, $R^5$, $R^6$ and $R^7$ are each independently hydrogen or $C_{1-6}$ alkyl;

$A^1$ and $A^2$ are each independently a direct bond or $CH_2$;

$R^8$ and $R^9$ are hydrogen; and $R^{10}$, $R^{11}$, $R^{12}$, $R^{13}$, $R^{14}$, $R^{15}$, $R^{16}$ and $R^{17}$ are each independently hydrogen, halo, $C_{1-6}$ alkyl, $C_{2-6}$ alkenyl, $C_{2-6}$ alkynyl, $C_{1-6}$ alkyloxy, $C_{2-6}$ alkenylmethoxy, $C_{1-6}$ alkylthio, trifluoromethyl, hydroxy, amino, mono or di($C_{1-6}$ alkyl)amino, arylamino, (aryl $C_{1-6}$ alkyl)amino, cyano, nitro, aryl, aryloxy, aryl $C_{1-6}$ alkyloxy, $C_{1-6}$ alkyloxy-$C_{1-6}$ alkyl or a radical of formula $$-C_sH_{2s}-(NH)_p-X-(Y)_q-L \qquad (a)$$

said s being 0 or an integer of from 1 to 6 inclusive;
said p and q being independently 0 or the integer 1;
said X being $>C=O$; $>C=S$; or $-S(=O)_2-$;
said Y being NH or O; and
said L being hydrogen, $C_{1-6}$ alkyl, aryl or aryl-$C_{1-6}$ alkyl; or two vicinal radicals of $R^{10}$, $R^{11}$, $R^{12}$ and $R^{13}$ and of $R^{14}$, $R^{15}$, $R^{16}$ and $R^{17}$ may complete a phenyl-, cyclohexene, dioxanyl- or dioxolanyl ring provided that L is other than hydrogen when X is $-S(=O)_2-$;
provided that not more than two radicals of $R^{10}$, $R^{11}$, $R^{12}$ and $R^{13}$ or of $R^{14}$, $R^{15}$, $R^{16}$ and $R^{17}$ are amino, mono- or di($C_{1-6}$ alkyl)amino, arylamino, (aryl-$C^{1-6}$ alkyl)amino, nitro, aryl, aryloxy or a radical of formula (a);
wherein aryl as used in the foregoing definitions is phenyl optionally substituted with up to three substituents each independently selected from the group consisting of halo, lower alkyl, lower alkyloxy, lower alkylthio, trifluoromethyl, nitro and amino.

4. A pharmaceutical composition for the treatment and/or prevention of disorders of the coronary vascular system in patients suffering from same, containing a pharmaceutically acceptable inert carrier and a pharmaceutically effective amount of $\alpha,\alpha'$-[iminobis(methylene)]bis[3,4-dihydro-2H-1-benzopyran-2-methanol], a pharmaceutically acceptable acid addition salt or a stereochemically isomeric form thereof.

5. A method for treating and/or preventing disorders of the coronary vascular system in warm-blooded animals suffering from same, which method comprises the systemic administration to warm-blooded animals of a pharmaceutically effective amount of a compound having the formula a pharmaceutically acceptable acid addition salt or a stereochemically isomeric form thereof, wherein $R^1$ is hydrogen, $C_{1-6}$ alkyl, aryl, aryl-$C_{1-6}$ alkyl, $C_{1-12}$ alkylcarbonyl or arylcarbonyl;

$R^2$ and $R^3$ are each independently hydrogen, $C_{1-12}$ alkylcarbonyl or arylcarbonyl;

$R^4$, $R^5$, $R^6$ and $R^7$ are each independently hydrogen or $C_{1-6}$ alkyl;

$A^1$ and $A^2$ are each independently a direct bond, or $CH_2$;

$R^8$ and $R^9$ are hydrogen; and $R^{10}$, $R^{11}$, $R^{12}$, $R^{13}$, $R^{14}$, $R^{15}$, $R^{16}$ and $R^{17}$ are each independently hydrogen, halo, $C_{1-6}$ alkyl, $C_{2-6}$ alkenyl, $C_{2-6}$ alkynyl, $C_{1-6}$ alkyloxy, $C_{2-6}$ alkenylmethoxy, $C_{1-6}$ alkylthio, trifluoromethyl, hydroxy, amino, mono or di($C_{1-6}$ alkyl)amino, arylamino, (aryl $C_{1-6}$ alkyl)amino, cyano, nitro, aryl, aryloxy, aryl $C_{1-6}$ alkyloxy, $C_{1-6}$ alkyloxy-$C_{1-6}$ alkyl or a radical of formula $$-C_sH_{2s}-(NH)_p-X-(Y)_q-L \qquad (a)$$

said s being 0 or an integer of from 1 to 6 inclusive;
said p and q being independently 0 or the integer 1;
said X being $>C=O$; $>C=S$; or $-S(=O)_2-$;
said Y being NH or O; and
said L being hydrogen, $C_{1-6}$ alkyl, aryl or aryl-$C_{1-6}$ alkyl; or two vicinal radicals of $R^{10}$, $R^{11}$, $R^{12}$ and $R^{13}$ and of $R^{14}$, $R^{15}$, $R^{16}$ and $R^{17}$ may complete a phenyl-, cyclohexene, dioxanyl- or dioxolanyl ring provided that L is other than hydrogen when X is $-S(=O)_2-$;
provided that not more than two radicals of $R^{10}$, $R^{11}$, $R^{12}$ and $R^{13}$ or of $R^{14}$, $R^{15}$, $R^{16}$ and $R^{17}$ are amino, mono- or di($C_{1-6}$ alkyl)amino, arylamino, (aryl-$C^{1-6}$ alkyl)amino, nitro, aryl, aryloxy or a radical of formula (a);
wherein aryl as used in the foregoing definitions is phenyl optionally substituted with up to three substituents each independently selected from the group consisting of halo, lower alkyl, lower alkyloxy, lower alkylthio, trifluoromethyl, nitro and amino.

6. A method for treating and/or preventing disorders of the coronary vascular system in warm-blooded animals suffering from same, which method comprises the systemic administration of warm-blooded animals of a pharmaceutically effective amount of $\alpha,\alpha'$-[iminobis(methylene)]bis[3,4-dihydro-2H-1-benzopyran-2-methanol], a pharmaceutically acceptable acid addition salt or a stereochemically isomeric form thereof.

7. A chemical compound according to claim 1 wherein $R^{10}$ through $R^{17}$ are each independently hydrogen, halo, $C_{1-6}$ alkyl, $C_{1-6}$ alkyloxy, $C_{2-6}$ alkenylmethoxy, hydroxy, cyano, or aryl $C_{1-6}$ alkyloxy; or two vicinal radicals of $R^{10}$ through $R^{13}$ and of $R^{14}$ through $R^{17}$ may complete a phenyl or cyclohexene ring; provided that no more than two of $R^{10}$ through $R^{17}$ are other than hydrogen.

8. A chemical compound according to claim 1 wherein $R^{10}$ through $R^{17}$ are hydrogen.

9. A pharmaceutical composition according to claim 3 wherein $R^{10}$ through $R^{17}$ are each independently hydrogen, halo, $C_{1-6}$ alkyl, $C_{1-6}$ alkyloxy, $C_{2-6}$ alkenylmethoxy, hydroxy, cyano, or aryl $C_{1-6}$ alkyloxy; or two vicinal radicals of $R^{10}$ through $R^{13}$ and of $R^{14}$ through $R^{17}$ may complete a phenyl or cyclohexene ring; provided that no more than two of $R^{10}$ through $R^{17}$ are other than hydrogen.

10. A pharmaceutical composition according to claim 3 where $R^{10}$ through $R^{17}$ are hydrogen.

11. A method according to claim 5 wherein $R^{10}$ through $R^{17}$ are each independently hydrogen, halo, $C_{1-6}$ alkyl, $C_{1-6}$ alkyloxy, $C_{2-6}$ alkenylmethoxy, hydroxy, cyano, or aryl $C_{1-6}$ alkyloxy; or two vicinal radicals of $R^{10}$ through $R^{13}$ and of $R^{14}$ through $R^{17}$ may complete a phenyl or cyclohexene ring; provided that no more than two of $R^{10}$ through $R^{17}$ are other than hydrogen.

12. A method according to claim 5 wherein $R^{10}$ through $R^{17}$ are hydrogen.

* * * * *

UNITED STATES PATENT AND TRADEMARK OFFICE
CERTIFICATE OF CORRECTION

PATENT NO. : 4,654,362

DATED : March 31, 1987

INVENTOR(S) : Guy R. E. Van Lommen et al.

It is certified that error appears in the above-identified patent and that said Letters Patent is hereby corrected as shown below:

Column 29, line 19, delete "ortwo" and insert --or two--.

Column 29, lines 48-55, delete " 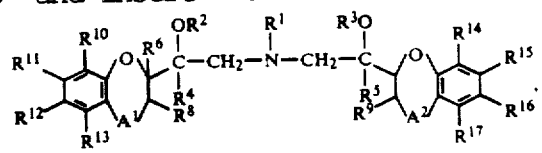 "

and insert -- 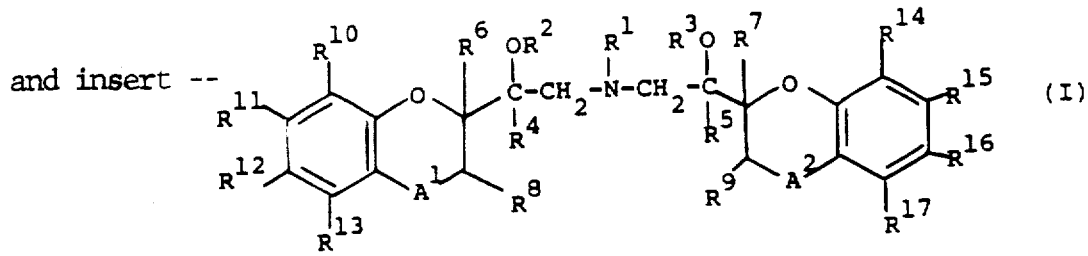

Signed and Sealed this

Tenth Day of January, 1989

Attest:

DONALD J. QUIGG

Attesting Officer

Commissioner of Patents and Trademarks